US00PP13691P29

(12) United States Plant Patent
Hofmann

(10) Patent No.: US PP13,691 P2
(45) Date of Patent: Apr. 1, 2003

(54) NEW GUINEA IMPATIENS PLANT NAMED 'FISIMP 130'

(76) Inventor: Birgit Hofmann, Gassenweg 29, 56170 Bendorf (DE)

( * ) Notice: Subject to any disclaimer, the term of this patent is extended or adjusted under 35 U.S.C. 154(b) by 0 days.

(21) Appl. No.: 10/080,602

(22) Filed: Feb. 22, 2002

(51) Int. Cl.[7] ..... A01H 5/00
(52) U.S. Cl. ..... Plt./318
(58) Field of Search ..... Plt./318

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of New Guinea Impatiens plant named 'Fisimp 130', characterized by its outwardly spreading, rounded and uniformly mounded plant habit; freely branching and freely flowering habit; large rounded light pink and red bi-colored flowers that are positioned above and beyond the foliage; and dark green-colored leaves.

1 Drawing Sheet

BOTANICAL CLASSIFICATION/CULTIVAR DESIGNATION

*Impatiens hawkeri* cultivar Fisimp 130.

BACKGROUND OF THE INVENTION

The present Invention relates to a new and distinct cultivar of New Guinea Impatiens plant, botanically known as *Impatiens hawkeri*, and hereinafter referred to by the name 'Fisimp 130'.

The new Impatiens is a product of a planned breeding program conducted by the Inventor in Hillscheid, Germany. The objective of the breeding program is to develop new moderately compact Impatiens cultivars that flower relatively early with large rounded flowers and attractive flower colors.

The new Impatiens originated from a cross made by the Inventor in July, 1998 of the *Impatiens hawkeri* cultivar Neptis, disclosed in U.S. Plant Pat. No. 10,321, as the female, or seed, parent with the *Impatiens hawkeri* cultivar Woya, disclosed in U.S. Plant Pat. No. 10,858, as the male, or pollen, parent. The cultivar Fisimp 130 was discovered and selected by the Inventor as a flowering plant within the progeny of the stated cross in a controlled environment in Moncarapacho, Portugal in March, 1999.

Asexual reproduction of the new cultivar by terminal cuttings taken in Moncarapacho, Portugal, since March, 1999, has shown that the unique features of this new Impatiens are stable and reproduced true to type in successive generations.

SUMMARY OF THE INVENTION

The following traits have been repeatedly observed and are determined to be the unique characteristics of 'Fisimp 130'. These characteristics in combination distinguish 'Fisimp 130' as a new and distinct Impatiens cultivar:

1. Outwardly spreading, rounded and uniformly mounded plant habit.

2. Freely branching and freely flowering habit.

3. Large rounded light pink and red bi-colored flowers that are positioned above and beyond the foliage.

4. Dark green-colored leaves.

Plants of the new Impatiens are most similar to plants of the female parent, the cultivar Neptis. In side-by-side comparisons conducted by the Inventor in Hillscheid, Germany, plants of the new Impatiens differed from plants of the cultivar Neptis in the following characteristics:

1. Plants of the new Impatiens were not as vigorous and had shorter internodes than plants of the cultivar Neptis.

2. Plants of the new Impatiens had smaller leaves than plants of the cultivar Neptis.

3. Plants of the new Impatiens flowered earlier than plants of the cultivar Neptis.

4. Flower color of plants of the new Impatiens and the cultivar Neptis differed in flower coloration.

Plants of the new Impatiens can be compared to plants of the male parent, the cultivar Woya. In side-by-side comparisons conducted by the Inventor in Hillscheid, Germany, plants of the new Impatiens differed from plants of the cultivar Woya in the following characteristics:

1. Plants of the new Impatiens were not as compact as plants of the cultivar Woya.

2. Plants of the new Impatiens had darker green-colored foliage than plants of the cultivar Woya.

3. Flowers of plants of the new Impatiens were light pink and red bi-colored whereas flowers of plants of the cultivar Woya were pink-colored.

Plants of the new Impatiens and the cultivar Fisimp 149, U.S. Plant Patent application filed concurrently, differ in flower coloration.

Plants of the new Impatiens can also be compared to plants of the cultivar Danharras, not patented. In side-by-side comparisons conducted by the Inventor in Hillscheid, Germany, plants of the new Impatiens differed from plants of the cultivar Danharras in the following characteristics:

1. Plants of the new Impatiens had more narrow and lighter green-colored leaves than plants of the cultivar Danharras.

2. Flowers of plants of the new Impatiens and the cultivar Danharras differed in flower coloration.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a side perspective view of a typical flowering plant of 'Fisimp 130' grown in a container.

DETAILED BOTANICAL DESCRIPTION

The cultivar Fisimp 130 has not been observed under all possible environmental conditions. The phenotype may vary somewhat with variations in environment such as temperature and light intensity, without, however, any variance in genotype.

The aforementioned photographs, following observations and measurements describe plants grown in Langley, British Columbia, Canada, under commercial practice in a greenhouse. Rooted young plants were planted in 17.5-cm containers during the spring and the aforementioned photograph and following observations and measurements were taken during the summer about 17 weeks later. During the production of the plants, day temperatures ranged from 21 to 24° C. and night temperatures were about 17 to 18° C. In the following description, color references are made to The Royal Horticultural Society Colour Chart, 1995 Edition, except where general terms of ordinary dictionary significance are used.

Botanical classification: *Impatiens hawkeri* cultivar Fisimp 130.

Parentage:

*Female parent.*—*Impatiens hawkeri* cultivar Neptis, disclosed in U.S. Plant Pat. No. 10,321.

*Male parent.*—*Impatiens hawkeri* cultivar Woya, disclosed in U.S. Plant Pat. No. 10,858.

Propagation:

*Type cutting.*—Terminal tip cuttings.

*Time to initiate roots.*—Summer: About 8 to 9 days at 24° C. Winter: About 10 days at 21° C.

*Tme to produce a rooted cutting.*—Summer: About 15 days at 24° C. Winter: About 18 days at 21° C.

*Root description.*—Numerous, fibrous, and freely branching; 159A in color.

Plant description:

*General appearance.*—Outwardly spreading, low, rounded and uniformly mounded plant growth habit; freely branching habit, dense and bushy appearance; freely flowering. Moderately vigorous.

*Crop time.*—From a rooted cutting, about 10 to 11 weeks are required to produce finished flowering plants in 12-cm containers.

*Plant height.*—*About* 21 cm.

*Plant diameter or spread.*—About 48.8 cm.

*Lateral branches.*—Quantity per plant: About 12. Length: About 20 cm. Diameter: About 8 mm. Internode length: About 5.25 cm. Color: 179A to 181A.

*Foliage description.*—Arrangement: Primarily in whorls. Length: About 12.1 cm. Width: About 4.5 cm. Shape: Elliptic. Apex: Acuminate. Base: Acute. Margin: Serrulate with ciliation. Texture: Smooth, slightly rugose; glabrous. Color: Young foliage, upper surface: 139A. Young foliage, lower surface: 185B. Fully expanded foliage, upper surface: 139A. Fully expanded foliage, lower surface: 185B to 185C. Venation, upper surface: 46A. Venation, lower surface: 53A. Petiole: Length: About 2.6 cm. Diameter: About 4.5 mm. Color: Upper surface: 53C. Lower surface: 53B.

Flower description:

*Flower type and flowering habit.*—Single; large rounded light pink and red-colored flowers. Freely and continuously flowering; usually about 8 to 11 flowers and flower buds per lateral branch. Flowers flat and positioned above and beyond the foliage and typically face parallel to the leaf canopy. Petals not persistent; gynoecium persistent. Flowers not fragrant.

*Flower longevity.*—Flowers last about 8 to 9 days on the plant.

*Flowering season.*—Year-round under greenhouse conditions. Plants begin flowering about 9 to 9.5 weeks after planting.

*Flower buds.*—Length: About 2 cm. Diameter: About 1.7 cm. Shape: Ovoid. Color: 46C to 46D.

*Flower length.*—6.6 cm.

*Flower width.*—About 6.2 cm.

*Flower depth.*—About 1 cm.

*Petals.*—Quantity: Five per flower, imbricate. Length: Banner petals: About 2.7 cm. Lateral and base petals: About 3 cm. Width: Banner petal: About 5.2 cm. Lateral and base petals: About 4.3 cm. Shape: Roughly cordate. Apex: Emarginate. Base: Attenuate. Margin: Entire. Aspect: Mostly flat to slightly upright. Texture: Smooth; satiny. Color: When opening, upper surface: Ground color, 62D to almost 155D; center of banner petal and fine longitudinal lines on lateral and base petals, 52A. Towards base of petals or eye, close to 57B. When opening, lower surface: 52A. Fully opened, upper surface: Ground color, 62D to almost 155D; center of banner petal and fine longitudinal lines on lateral and base petals, 46C to 52A. Towards base of petals or eye, close to 57B. Coloration does not fade with subsequent development. Fully opened, lower surface: 52A to 52B.

*Spur.*—Quantity: One per flower. Length: About 5.3 cm. Diameter: At apex: About 0.5 mm. At flower: About 3 mm. Aspect: Curved. Color: Towards the flower, 49B to 49C; towards the apex, 145C.

*Peduncles.*—Length: About 6.5 cm. Diameter: About 2 mm. Strength: Strong, flexible. Angle: About 45° from the lateral branch. Color: 144C, occasionally overlain with anthocyanin, 180D.

*Reproductive organs.*—Androecium: Stamen number: Five fused at anthers, hooded; filaments free. Anther length: About 5 mm. Anther shape: Obovate. Anther color: 54A. Pollen amount: Moderate. Pollen color: 8D. Gynoecium: Pistil quantity: One per flower. Pistil length: About 5.5 mm. Stigma color: 53D. Style color: 53D. Ovary: Five-celled. Ovary color: Initially 147A; with development, 87A.

*Seed/fruit.*—Seed and fruit development has not been observed.

Disease/pest resistance: Plants of the new Impatiens have not been observed to be resistant to pathogens and pests common to Impatiens.

It is claimed:

1. A new and distinct cultivar of New Guinea Impatiens plant named 'Fisimp 130', as illustrated and described.

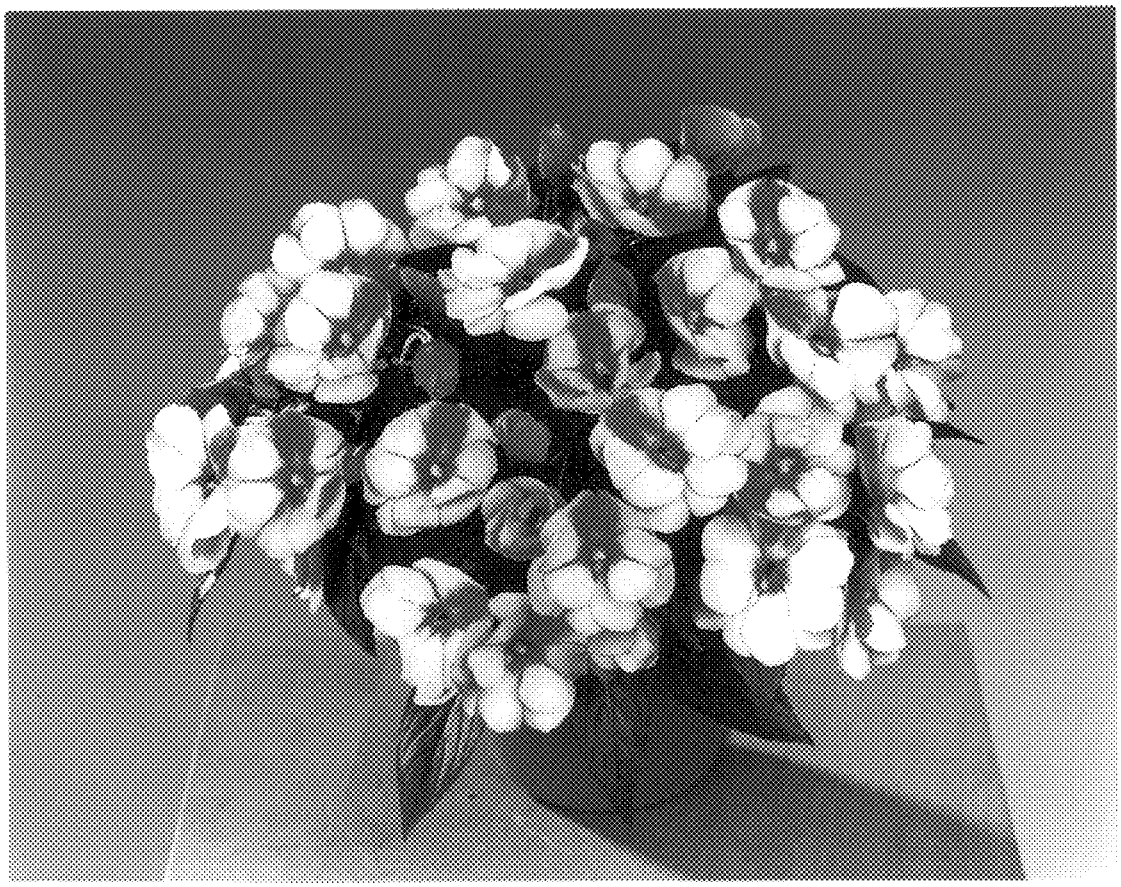

* * * * *